United States Patent [19]

Arndt et al.

[11] Patent Number: 4,545,803

[45] Date of Patent: Oct. 8, 1985

[54] SOIL TREATING METHOD AND COMPOSITION FOR CONSERVING NITROGEN IN SOIL

[75] Inventors: Kim E. Arndt, Pittsburg; Richard B. Rogers; Ronald W. McCormick, both of Concord, all of Calif.

[73] Assignee: The Dow Chemical Company, Midland, Mich.

[21] Appl. No.: 624,429

[22] Filed: Jun. 25, 1984

[51] Int. Cl.$^4$ ............................ C05G 3/08; C07F 3/06
[52] U.S. Cl. ............................................. 71/27; 71/28; 71/902; 71/DIG. 1; 556/38
[58] Field of Search .................... 260/429 R, 429.9; 71/11, 28, 27, 902, DIG. 1

[56] References Cited

U.S. PATENT DOCUMENTS 3,635,690  1/1972  Griffith ............................... 71/27 X Primary Examiner—Ferris H. Lander
Attorney, Agent, or Firm—S. Preston Jones; Ronald G. Brookens

[57] ABSTRACT

Certain metal salts of certain substituted pyrazole dithiocarbamates are employed as the active nitrification inhibitor in the presence of reduced nitrogen fertilizers. Compositions containing these salts can be applied to the surface of the soil and can remain on said soil surface for up to 3 days or more without mechanical incorporation into the soil and retain at least about 70 percent of the pyrazole as the salt in the composition.

20 Claims, No Drawings

SOIL TREATING METHOD AND COMPOSITION FOR CONSERVING NITROGEN IN SOIL

BACKGROUND OF THE INVENTION

The majority of plants obtain most or all of their nitrogen requirements from the soil. The adequate provision of nutrient nitrogen in soil for plant growth is one of the foremost agronomic problems. The nitrogen in the soil is found to occur primarily in three forms: organic nitrogen, ammonium nitrogen and nitrate nitrogen, of which ammonium nitrogen and nitrate nitrogen are the primary forms utilized by plants. This nitrogen is absorbed by plants in solution from the soil in the form of ammonium ions and nitrate ions.

The ammonium nitrogen in the soil occurs principally as colloidal-bound nitrogen, only very small quantities of the ammonium form of soil nitrogen are lost from the feeding zone of the plants by leaching.

The nitrate nitrogen in the soil is derived from the oxidation or nitrification of ammonium nitrogen by soil bacteria or by the addition of inorganic nitrate fertilizers such as ammonium nitrate, sodium nitrate, potassium nitrate and calcium nitrate. The inorganic nitrate compounds are readily soluble in water and the aqueous soil medium. When so dissolved, the nitrate nitrogen largely exists as the nitrate ion.

The nitrogen contained in the nitrate, in contrast to ammonium nitrogen, is not adsorbed by the sorption carriers of the soil. A further discussion of the nature of this nitrogen problem in agriculture is set forth in U.S. Pat. No. 3,135,594.

Because of the anionic nature of this nitrate ion, nitrate nitrogen is rapidly leached by rainfall and irrigation and readily lost from the feeding zone of the plants. Further, the nitrate nitrogen is reduced by many soil bacteria to nitrogen gas. The latter process is known as denitrification and accounts for an additional loss of large quantities of nitrate nitrogen from the soil. The yearly loss from leaching and denitrification amounts to from 20 to 80 percent of the nitrate nitrogen found in the soil.

To overcome the loss of ammonium nitrogen in the soil by nitrification, it is the practice to add to the soil a nitrification inhibitor.

Representative nitrification inhibitors and their use can be found in U.S. Pat. Nos. 3,135,594, 3,494,757 and 3,635,690 and British Pat. No. 1,592,516.

While the known inhibitors are effective in reducing nitrification, they, for the most part, have a major drawback in that they must be incorporated into the soil within a very short period of time, i.e., a few minutes to a few hours in order to avoid losses of the inhibitor to the air. This requirement for quick incorporation hinders and/or restricts the use of nitrification inhibitors in agronomic practices where no till or minimum till is employed and in those areas where fertilizers are added and incorporation is delayed.

SUMMARY OF THE INVENTION

The present invention is directed to methods and compositions useful in crop culture, and is particularly concerned with new agronomical practices and compositions for conserving nitrogen in soil by suppressing the nitrification of ammonium nitrogen therein. The active agent of the compositions employed in such methods is a metal salt of a bis(pyrazole-1-carbodithioate) corresponding to the formula

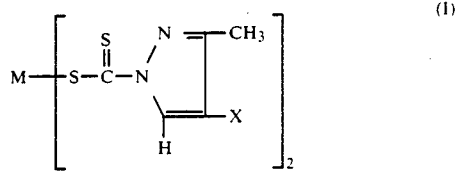

wherein M represents cobalt, copper, iron, manganese, nickel or zinc and X represents hydrogen, bromo, chloro or methyl.

The pyrazole compounds which are a part of the 1-carbodithioate are 3-methylpyrazole, 4-bromo-3-methylpyrazole, 4-chloro-3-methylpyrazole and 3,4-dimethylpyrazole.

While the active pyrazoles of the present invention are normally depicted as shown in Formula I, it is believed that these compounds also exist in two additional isomeric forms. These isomers can be depicted as follows:

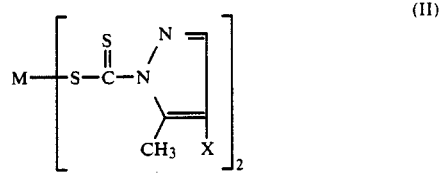

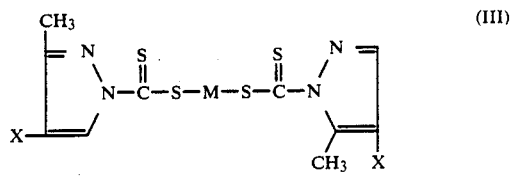

wherein M and X are as above set forth.

It is further believed that the product obtained in the preparation of Formula I is a mixture of the three isomers and the depiction of either one of the isomers should be taken as the inclusion of all three isomers.

The method of the present invention comprises applying to soil a composition which contains, as the active nitrification inhibitor, a metal salt of a bis(pyrazole-1-carbodithioate) as defined above (hereinafter pyrazole compound). A further feature of the method of the present invention is that the pyrazole compound in admixture with a reduced nitrogen fertilizer can be applied to the surface of soil where it can remain without incorporation into the soil for a period of up to 3 days or more, with at least about 70 percent of the pyrazole remaining. After administration subsequent irrigation or rainfall can distribute the pyrazole compound throughout the soil.

The expression "soil" is employed herein in its broadest sense to be inclusive of all conventional "soils", as defined in Webster's New International Dictionary, Second Edition, unabridged, published in 1937, G. C. Merriam Co., Springfield, Mass. Thus, the term refers to any substance or medium in which plants may take root and grow, and is intended to include not only earth, but also compost, manure, muck, sand, synthetic growth mediums such as vermiculite and pearlite and the like, adapted to support plant growth.

By the practice of this invention, the nitrification of ammonium nitrogen in the soil to nitrate nitrogen is suppressed, thereby preventing the rapid loss of ammonium nitrogen from the soil. Furthermore, by proper distribution of the pyrazole compound this action of inhibiting the transformation of ammonium nitrogen to nitrate nitrogen is effective over a prolonged period of time. The ammonium nitrogen may arise from added ammonium nitrogen fertilizers or be formed in the soil by conversion of the organic nitrogen constituents found in soil or added thereto as components of organic fertilizers.

The expression "reduced nitrogen fertilizers" as employed in the present specification and claims, is understood in the art, as embracing both inorganic and organic nitrogenous materials containing nitrogen in the reduced state. Examples of known reduced nitrogen fertilizers include anhydrous ammonia, aqueous ammonia, inorganic ammonium salts such as ammonium phosphate, ammonium nitrate and ammonium sulfate, ammonium salts of organic acids, urea, cyanamide, guanidine nitrate, dicyandiamide, thiourea, urea-form and other nitrogen-containing organic chemical fertilizers as well as protein mixtures, animal tankages, green manure, fish products, crop residues, and other natural materials known to be sources of ammonium ions in soil.

The application of an effective, nitrification inhibiting, dosage of the pyrazole compound to the soil is essential for the practice of the present invention. In general, good results are obtained when the pyrazole compound is applied in the amount of from about 0.05 to about 10.0 pounds per acre of soil. The preferred amounts to be employed are dependent upon the particular situation. Thus, in determining the amount to be employed, consideration is necessary as to the soil pH, soil organic matter, temperature, soil type and time of application. By dispersing very large dosages to soil, a prolonged inhibition of nitrification can be obtained over a period of many months. The concentration of the active pyrazole compound is eventually reduced to a minimum by decomposition in the soil.

In one method for carrying out the present invention, the pyrazole compound is distributed to the soil in a broadcast application such as by spraying, dusting, distributing in irrigation water, etc. In such application, the pyrazole compound is supplied in amounts of from about 0.05 to about 10.0 pounds per acre.

In another method for carrying out the present invention, the pyrazole compound is administered to the soil in a band or row application. In such application, administration is made with or without carrier in amounts sufficient to supply to the soil a concentration of the pyrazole compound which can be as high as 10 pounds per acre or more.

In one embodiment of the present invention, the pyrazole compound is distributed throughout the soil prior to seeding or transplanting the desired crop plant.

In another embodiment, the soil in the root zone of growing plants is treated with the pyrazole compound in an amount effective to inhibit nitrification but sublethal to plant growth.

In a further embodiment, the pyrazole compound can be applied following harvest or after following to prevent rapid loss of ammonium nitrogen and to build up the ammonium nitrogen formed by conversion of organic nitrogen compounds. Such practice conserves the soil nitrogen for the following growing season. In such application the upper limit is primarily an economic consideration.

Additionally, the pyrazole compound can be applied prior to, subsequent to or simultaneous with the application of a reduced nitrogen fertilizer. Such practice prevents the rapid loss of the ammonium nitrogen added as fertilizer and the ammonium nitrogen formed from the organic reduced nitrogen in fertilizers by the action of soil bacteria. In a preferred procedure, the pyrazole compound is employed as a solid or liquid composition comprising a reduced nitrogen fertilizer in intimate admixture with the pyrazole compound.

As indicated above, the present method embraces distributing the pyrazole compound as a constituent in liquid or solid fertilizer compositions. In such practice, the pyrazole compound is admixed with the fertilizer and such mixture can be modified with one or more additaments or soil treating adjuvants to formulate the mixtures employing conventional procedures as wettable powders, emulsifiable concentrates, dust, granular formulations or oil or water flowable emulsion concentrates. In preparing such formulations, the pyrazole compound/fertilizer mixture is extended with adjuvants including water, petroleum distillates or other liquid carriers, surface-active dispersing agents and inert finely-divided solids. Preferred adjuvants are surface-active dispersing agents and inert finely-divided solids; these adjuvants cooperate with the pyrazole compound so as to facilitate the practice of the present invention and to obtain an improved result. These compositions may also contain as additional adjuvants one or more other biologically active materials such as herbicides, insecticides, fungicides, miticides, bactericides, nematocides, and the like. The only requirement for these added materials is that they be both chemically and biologically compatible with the pyrazole compound.

The concentration of the pyrazole compound in the compositions can vary considerably provided the required nitrification inhibition dosage of the effective agent is supplied to the soil. In general, good results are obtained when employing liquid compositions containing from about 0.05 to about 5.0 percent by weight of the pyrazole compound; in some operations, however, compositions containing amounts of pyrazole compound in excess of 5.0 percent, such as from 5 to 98 percent of the active pyrazole compound by weight of composition are conveniently employed, as for example, in row or band application. With solids, good results are usually obtained with compositions containing from 0.05 to 5.0 percent or more by weight of pyrazole compound. In some circumstances, such as in high-intensity application, however, it is preferred to employ solid compositions containing as much as from 5 to 98 percent or more by weight of the pyrazole compound. Liquid or solid compositions in which the pyrazole compound is present in higher concentration can be utilized as such or can be employed as concentrate compositions to be diluted to prepare actual treating compositions.

The liquid compositions containing active agent, i.e., the pyrazole compound, can be prepared by admixing one or more of the active agents with water or an organic solvent, with or without the aid of a suitable surface-active dispersing agent or emulsifying agent, and admixing this mixture in an aqueous solution of the desired fertilizer.

Suitable organic solvents include acetone, diisobutylketone, methanol, ethanol, isopropyl alcohol, diethyl ether, toluene, methylene chloride, chlorobenzene and the petroleum distillates. The preferred organic solvents are those which are of such volatility that they leave little permanent residue in the growth media.

Dispersing and emulsifying agents which can be employed in liquid compositions include condensation products of alkylene oxides with phenols and organic acids, alkyl aryl sulfonates, polyoxyalkylene derivatives of sorbitan esters, complex ether alcohols, mahogany soaps and the like. The surface-active agents are generally employed in the amount of from 1 to 20 percent by weight of the pyrazole compound.

Solid compositions containing the active agent can be prepared by admixing the pyrazole compound, dispersed in a volatile organic solvent, with the solid fertilizer. In another procedure, the solid fertilizer can be mechanically ground with a dispersion of the pyrazole compound in a solvent and the resulting mixture prilled, granulated or otherwise formed into the desired form. After coating the solvent is vaporized off. In an additional procedure, solid granules of the fertilizer are treated with a sticking agent such as mineral oil and then coated with a dispersion of the pyrazole compound in a solvent.

These solid compositions may, if desired also contain an alkyl aryl sulfonate or other surface-active dispersing agent. Depending upon the proportions of ingredients, these compositions can be employed without further modification or be considered as concentrates and subsequently further diluted with conventional solid carriers such as talc, chalk, gypsum, clays, or the like to obtain the desired treating composition. Furthermore, such concentrate compositions can be dispersed in water with or without added dispersing agent or agents to prepare aqueous soil treating compositions.

In these fertilizer compositions, it is desirable that the pyrazole compound be present in an amount of at least about 0.05 percent by weight based on the weight of the nitrogen present in the fertilizer as reduced nitrogen and can be present in amounts as high as 95 percent by weight of the reduced nitrogen in the fertilizer. Generally, though, amounts of pyrazole compound in excess of about 5.0 percent yield no greater advantage and are therefore seldom used. Thus, when a fertilizer composition contains both reduced nitrogen and other forms of nitrogen, such as in the case of ammonium nitrate fertilizer compositions, the amount of pyrazole compound is based on the weight of nitrogen present in the ammonium component.

The novel pyrazole compounds employed in the practice of the present invention can be prepared employing procedures similar to those taught in Trofimenko, The Journal of Organic Chemistry, Volume 33, No. 2, February 1968, pages 890–892 wherein an aqueous solution of an alkali metal pyrazole-1-carbodithioate is mixed with the appropriate metal ion.

The following examples illustrate the invention but should not be construed as limiting the scope of the invention.

EXAMPLE I

Zinc bis (3-methylpyrazole-1-carbodithioate)

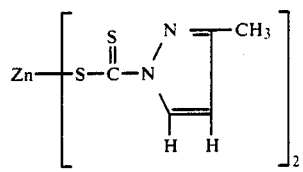

To a solution of 7.6 grams of zinc chloride in 100 milliliters of deionized water was added at once a solution of 20 grams of the sodium salt of 3-methylpyrazole-1-carbodithioate in 150 milliliters of deionized water with vigorous stirring. The product precipitated immediately as a yellow solid. The product was collected by filtration, dried and recovered in a yield of 14.5 grams (70 percent of theoretical). The product melted at 151°–153° C., with decomposition. Upon analysis, the product was found to have carbon, hydrogen and nitrogen contents of 31.39, 2.60 and 14.62 percent, respectively, as compared with the theoretical contents of 31.62, 2.65 and 14.75 percent, respectively, as calculated for the above-named compound.

EXAMPLE II

Sodium salt of 3-methylpyrazole-1-carbodithioate

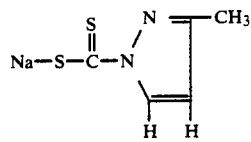

A slurry was prepared by admixing 1.5 grams of sodium hydride with 200 milliliters of dry tetrahydrofuran. To this slurry was slowly added, with stirring, 5.0 grams of 3-methylpyrazole. The solution thus formed was filtered and then an excess of carbon disulfide (4.65 grams) was added, at once with stirring. After 5 minutes, a yellow precipitate formed. Half of the solvent was removed in vacuo and the product was recovered by filtration. The product was washed with dry ether and dried. The desired product was recovered in a yield of 6.8 grams (62 percent of theoretical). The product melted at 254°–255° C., with decomposition. Upon analysis, the product was found to have carbon, hydrogen and nitrogen contents of 33.13, 2.71 and 15.39 percent, respectively, as compared with the theoretical contents of 33.32, 2.80 and 15.55 percent, respectively, calculated for the above-named compound.

EXAMPLE III

Zinc bis (3,4-dimethylpyrazole-1-carbodithioate)

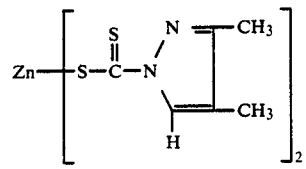

A mixture is prepared by admixing 7.9 grams of the sodium salt of 3,4-dimethylpyrazole-1-carbodithioate in 50 milliliters of deionized water. This mixture is added to a mixture of 2.6 grams of zinc chloride in 250 milliliters of deionized water. A precipitate formed immediately and the product was recovered by filtration and dried. The product was recovered in a yield of 6.2 grams (75 percent of theoretical). The product decomposed above 210° C. Upon analysis, the product was found to have carbon, hydrogen and nitrogen contents of 35.00, 3.42 and 13.85 percent, respectively as compared with the theoretical contents of 35.33, 3.46 and 13.74 percent, respectively, as calculated for the above-named compound.

EXAMPLE IV

Sodium salt of 3,4-dimethylpyrazole-1-carbodithioate

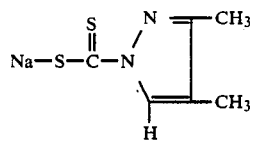

A slurry was prepared by admixing 2.2 grams of 60 percent sodium hydride (after washing, this amounts to 1.32 grams) with 75 milliliters of dry tetrahydrofuran. To this slurry was slowly added, with stirring, 5.0 grams of 3,4-dimethylpyrazole. The solution thus formed was filtered and then an excess of carbon disulfide (7.0 grams) was added, with stirring. After 10 minutes, a yellow precipitate formed. The product was recovered by filtration and washed with dry ether and dried. The desired product was recovered in a yield of 7.9 grams (78 percent of theoretical). The product decomposed at 275°–278° C. Upon analysis, the product was found to have carbon, hydrogen and nitrogen contents of 36.88, 3.54 and 14.31 percent, respectively, as compared with the theoretical contents of 37.10, 3.63 and 14.42 percent, respectively, as calculated for the above-named compound.

The reactions in the above Examples were carried out employing room temperatures and atmospheric pressures.

EXAMPLE V

A study was conducted to determine the stability of the zinc salt of bis(-3-methylpyrazole-1-carbodithioate) when coated onto urea prills.

One hundred gram portions of urea prills were placed into 600 milliliter (ml) beakers and rotated at a 45° angle. The zinc salt of bis(-3-methyl-pyrazole-1-carbodithioate) was dissolved in methylene chloride and sprayed as a fine mist onto the rotating urea prills. After the prills were evenly coated, the solvent was evaporated off with the aid of a hot air gun.

Two different formulations were prepared, one in which the coated prills contained about 0.05 percent (%) and the other about 0.1% of the pyrazole by weight based on the weight of nitrogen in the urea. Each formulation contained a different percentage of the base pyrazole compound. In one, the solution contained 59.4 milligrams (mg) and the other 118.8 mg of the pyrazole compound was present on the urea prills.

Two gram samples of each formulation were weighed into 1 inch diameter × ¼ inch deep round steel planchetts and placed into a 35° C.±1° C. circulating oven. Samples of each formulation were removed for assay each week for three weeks to determine the amount of pyrazole loss from the surface of the urea.

This loss was determined employing standard high pressure liquid chromatograph analysis techniques. The results of this analysis are set forth below in Table I.

TABLE I

| Zinc Bis(3-methylpyrazole-1-carbodithioate) Formulation Tested | Stability at 35° C. % Pyrazole remaining per gram of ammonium nitrogen at following time in weeks[a] | | | |
|---|---|---|---|---|
| | 0 | 1 | 2 | 3 |
| 0.05 | 0.052 (100) | 0.047 (90) | 0.042 (81) | 0.036 (69) |
| 0.10 | 0.106 (100) | 0.095 (89) | 0.092 (86) | 0.076 (71) |

[a]figure in ( ) is percent (%) of pyrazole remaining based on 0 day amount.

What is claimed is:

1. A zinc bis(pyrazole-1-carbodithioate) corresponding to the formula

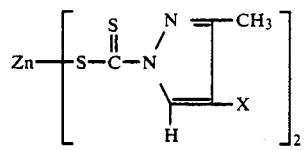

wherein X represents hydrogen, bromo, chloro or methyl.

2. The compound as defined in claim 1 which is zinc bis(3-methylpyrazole-1-carbodithioate).

3. The compound as defined in claim 1 which is zinc bis(3,4-dimethylpyrazole-1-carbodithioate).

4. The compound as defined in claim 1 which is zinc bis(4-bromo-3-methylpyrazole-1-carbodithioate).

5. The compound as defined in claim 1 which is zinc bis(4-chloro-3-methylpyrazole-1-carbodithioate).

6. A composition which comprises a reduced nitrogen fertilizer in admixture with from about 0.05 to about 98 percent by weight of an active agent which is a zinc bis(pyrazole-1-carbodithioate) which corresponds to the formula

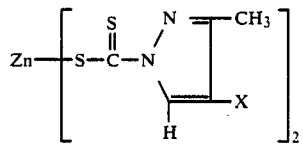

wherein X represents hydrogen, bromo, chloro or methyl.

7. The composition as defined in claim 6 wherein the active agent is zinc bis(3-methylpyrazole-1-carbodithioate).

8. The composition as defined in claim 6 wherein the active agent is zinc bis(3,4-dimethylpyrazole-1-carbodithioate).

9. The composition as defined in claim 6 wherein the active agent is zinc bis(4-bromo-3-methylpyrazole-1-carbodithioate).

10. The composition as defined in claim 6 wherein the active agent is zinc bis(4-chloro-3-methylpyrazole-1-carbodithioate).

11. A method for treating soil to inhibit the conversion therein of ammonium nitrogen to nitrate and nitrite nitrogen and to prevent rapid loss of ammonium nitrogen therefrom which comprises applying to soil a nitrification suppressing amount of a composition comprising a reduced nitrogen fertilizer in admixture with from about 0.05 to about 98 percent by weight of an active agent which is a zinc bis(pyrazole-1-carbodithioate) which corresponds to the formula

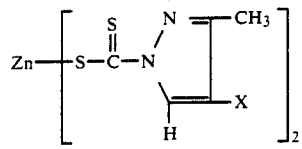

wherein X represents hydrogen, bromo, chloro or methyl.

12. The method as defined in claim 11 wherein the active agent is zinc bis(3-methylpyrazole-1-carbodithioate).

13. The method as defined in claim 11 wherein the active agent is zinc bis(3,4-dimethylpyrazole-1-carbodithioate).

14. The method as defined in claim 11 wherein the active agent is zinc bis(4-bromo-3-methylpyrazole-1-carbodithioate).

15. The method as defined in claim 11 wherein the active agent is zinc bis(4-chloro-3-methylpyrazole-1-carbodithioate).

16. A nitrification inhibition-fertilizer composition useful for delayed incorporation into soil which comprises a reduced nitrogen fertilizer in admixture with from about 0.05 to about 98 percent of an active agent which is a zinc bis(pyrazole-1-carbodithioate) which corresponds to the formula

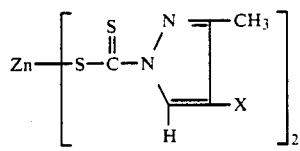

wherein X represents hydrogen, bromo, chloro or methyl.

17. The composition as defined in claim 16 wherein the active agent is zinc bis(3-methylpyrazole-1-carbodithioate).

18. The composition as defined in claim 16 wherein the active agent is zinc bis(3,4-dimethylpyrazole-1-carbodithioate).

19. The composition as defined in claim 16 wherein the active agent is zinc bis(4-bromo-3-methylpyrazole-1-carbodithioate).

20. The composition as defined in claim 16 wherein the active agent is zinc bis(4-chloro-3-methylpyrazole-1-carbodithioate).

* * * * *